(12) United States Patent
Fazi, Jr. et al.

(10) Patent No.: US 9,757,071 B1
(45) Date of Patent: Sep. 12, 2017

(54) SYSTEM AND METHOD FOR SUPPRESSING NOISE FROM ELECTROCARDIOGRAPHIC (ECG) SIGNALS

(71) Applicant: BAYER HEALTHCARE LLC, Indianola, PA (US)

(72) Inventors: Bruno Fazi, Jr., Pittsburgh, PA (US); Jason Palmer, Baden, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 15/142,737

(22) Filed: Apr. 29, 2016

(51) Int. Cl.
```
A61B 5/00      (2006.01)
A61B 5/044     (2006.01)
H03H 7/00      (2006.01)
H03H 7/01      (2006.01)
```

(52) U.S. Cl.
CPC .......... *A61B 5/7217* (2013.01); *A61B 5/044* (2013.01); *A61B 5/6804* (2013.01); *A61B 5/7203* (2013.01); *H03H 7/004* (2013.01); *H03H 7/0138* (2013.01)

(58) Field of Classification Search
CPC ....... A61B 5/72–5/7225; A61B 5/7217; A61B 5/0402–5/0472; A61B 18/16; A61B 5/04286
See application file for complete search history.

(56) References Cited

U.S. PATENT DOCUMENTS

| | | | |
|---|---|---|---|
| 1,888,139 A | 11/1932 | Nichols | |
| 3,580,243 A * | 5/1971 | Johnson | A61B 5/04004 128/902 |
| 3,826,246 A * | 7/1974 | Raddi | A61B 5/04286 600/382 |
| 3,960,141 A | 6/1976 | Bolduc | |
| 4,537,200 A | 8/1985 | Widrow | |
| 4,800,894 A | 1/1989 | Milani | |
| 5,392,784 A * | 2/1995 | Gudaitis | A61B 5/0428 128/902 |
| 5,494,036 A | 2/1996 | Uber, III et al. | |
| 6,148,229 A | 11/2000 | Morris, Sr. et al. | |
| 6,246,902 B1 | 6/2001 | Naylor et al. | |
| 6,339,718 B1 | 1/2002 | Zatezalo et al. | |

(Continued)

FOREIGN PATENT DOCUMENTS

WO    2013076619 A2    5/2013

OTHER PUBLICATIONS

Nakamura; et al., "A Comparative Evaluation Between Conditions of the Wrist Band Capacitively-Coupled ECG Recording through Signal-to-Noise Ratio", Jun. 22, 2007.

*Primary Examiner* — Michael Kahelin
(74) *Attorney, Agent, or Firm* — James R. Stevenson; Ryan Miller

(57) ABSTRACT

Systems and methods for suppressing electrical noise in an electrocardiogram (ECG) signal obtained by at least one electrode and displayed on an ECG monitor are disclosed. The system includes a conductive material distinct from the at least one electrode and configured to contact a surface of a patient, and filtering circuitry connected in series between the conductive material and ground. The filtering circuitry may be configured to filter to ground the electrical noise present within the patient before it is received by the at least one electrode and is prevented from distorting the ECG signal that is displayed on the ECG monitor.

20 Claims, 6 Drawing Sheets

(56) References Cited

U.S. PATENT DOCUMENTS

| | | |
|---|---|---|
| 6,643,537 B1 | 11/2003 | Zatezalo et al. |
| 6,958,053 B1 | 10/2005 | Reilly |
| 7,039,455 B1 | 5/2006 | Brosovich et al. |
| 8,634,901 B2 | 1/2014 | Callahan et al. |
| 2006/0002565 A1 | 1/2006 | Takemura |
| 2010/0191236 A1* | 7/2010 | Johnson ............... A61N 1/3718 606/41 |
| 2011/0275915 A1* | 11/2011 | Allgeyer ............ A61B 5/02427 600/324 |

* cited by examiner

SYSTEM AND METHOD FOR SUPPRESSING NOISE FROM ELECTROCARDIOGRAPHIC (ECG) SIGNALS

BACKGROUND

Field

The present disclosure relates to systems and methods for suppressing noise generated in an electrocardiographic (ECG) signal displayed on an ECG monitor due to external electrical equipment and, more particularly, to the suppression of noise generated in an ECG signal due to the presence of a powered injector in the vicinity of a patient.

Description of Related Art

Angiography is used generally in the detection and treatment of abnormalities or restrictions in blood vessels. In an angiographic procedure, one obtains a radiographic image of vascular structure with the assistance of a radiographic contrast medium (sometimes referred to simply as contrast) injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a monitor and recorded.

With reference to FIG. 1, in a typical medical imaging environment, a patient 100 is positioned in a room that includes an imaging system (not shown) as well as an injection system for injecting contrast and/or saline into the patient. One example of the injection system can include an injector 10 such as the MEDRAD® Stellant® CT Injection System available from the Radiology business of the Pharmaceutical Division of Bayer AG of Indianola, Pa., U.S.A. The injector 10 includes two syringe interfaces 20a and 20b to which two syringes 30a and 30b are removably attachable. Two drive members or pistons 40a and 40b operatively connect to plungers 50a and 50b slidably disposed in syringes 30a and 30b, respectively, to pressurize and inject the fluid therefrom into the patient 100 via a catheter 60 in fluid connection with syringes 30a and 30b. In addition, heater jackets 70a and 70b may be provided to maintain the fluid within the syringes 30a and 30b at a predetermined temperature. As shown in FIG. 1, such heater jackets 70a and 70b may each include an arcuate resistance heater portion configured to snap over the cylindrical body of the syringes 30a and 30b.

Further details of such injectors, control systems therefor, and injector protocols used therewith are described, for example, in U.S. Pat. Nos. 5,494,036, 6,339,718, 6,643,537, and 6,958,053, the disclosures of which are incorporated herein by reference.

In many instances, a patient scheduled for a scanning procedure may also be connected to a vital signs monitoring system, such as an ECG monitor 80, via a plurality of electrodes 82 attached to the skin of the patient. Each electrode 82 is connected via a lead 84 to the ECG monitor 80. Electrical noise/disturbance(s) are generated as a result of the use of the injector 10 and related equipment. For instance, electrical noise may be generated when the heater jackets 70a and 70b are turned on and off or due to an electrical disturbance (i.e., an ESD field) that may develop during the delivery of a fluid by the injector 10 due to the dissimilarities between the materials used for the barrels of the syringes 30a and 30b (e.g., plastic) and the plungers 50a and 50b (e.g., rubber). This electrical noise can be conveyed from the injector 10 and related equipment to the patient 100 via, for example, a fluid path 55 connecting the injector 10 to the catheter 60, which is conductive by virtue of the contrast medium or saline therein.

Unless this noise is safely routed to earth (low impedance), the noise will be picked up by the electrodes 82 of the ECG monitor 80. The noise/electrical disturbance then causes a distortion 86 of the ECG signals displayed on the ECG monitor 80. This is because the noise that is generated by the injector 10 and related equipment occupies the same part of the electromagnetic/frequency spectrum as the electrical (cardiac) signals generated by the heart of the patient 100.

Accordingly, a need exists for a system to safely route to ground noise generated by external electrical equipment, such as a powered injector system, positioned in proximity to a patient connected to an ECG monitor such that this noise is prevented from causing distortions in the ECG signals that are displayed on an ECG monitor.

SUMMARY

The present disclosure describes examples of filtering circuitry that, when in use, will be connected in series between ground and a non-magnetic, yet metallic, element, such as a wrist strap, configured to be positioned in contact with a patient. The filtering circuitry, which may employ an array of selected capacitors, allows the system to filter to ground the electrical noise generated by the injector and related equipment while the cardiac signals generated by the heart are still picked up by the electrodes of an ECG monitor and conveyed to the ECG monitor for display free of such noise.

Accordingly, provided is a system for suppressing electrical noise in an electrocardiogram (ECG) signal displayed on an ECG monitor. The system comprises: a conductive material provided in contact with a surface of a patient; and filtering circuitry connected in series between the conductive material and ground. The filtering circuitry is configured to filter to ground the electrical noise present within the patient.

In one example, the electrical noise may be generated by at least one electrical device located near the patient. In the examples described hereinafter, the at least one electrical device may be a powered injector and associated devices. However, this is not to be construed as limiting the present disclosure as the electrical noise may be generated by other electrical devices located near the patient such as a heating device, anesthesiology equipment, or electrosurgical equipment.

In an example of the present disclosure, the conductive material may be provided as a bracelet configured to be worn on a wrist of the patient. The conductive material may be provided on an interior surface of the bracelet with an exterior surface of the bracelet is made from an insulated material. In addition, the conductive material is desirably non-magnetic so as not to interfere with medical imaging equipment.

In one example, the filtering circuitry may be configured as an array of capacitors. The array of capacitors may include four capacitors, each of which having a capacitance of about 0.0047 µF.

A specific example of the system comprises a wrist strap positioned around the wrist of a patient and comprising a conductive material provided in contact with a surface of the patient; and filtering circuitry comprising an array of capacitors connected in series between the conductive material of the wrist strap and ground. The filtering circuitry is configured to filter to ground the electrical noise present within the patient that is generated by at least one electrical device located near the patient.

Also provided is a method for suppressing electrical noise in an electrocardiogram (ECG) signal displayed on an ECG monitor. The method comprises: providing a conductive material in contact with a surface of a patient; providing filtering circuitry connected in series between the conductive material and ground; and filtering to ground, with the filtering circuitry, electrical noise present within the patient.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

DETAILED DESCRIPTION

Figure 1:
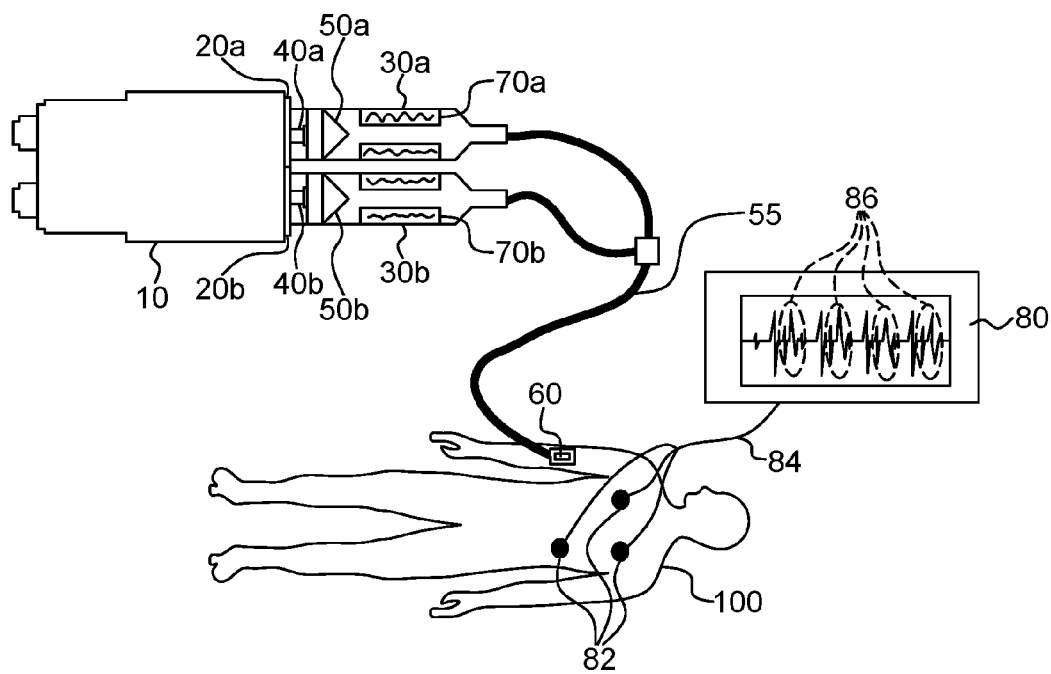
FIG. 1 is a schematic diagram of a conventional arrangement for delivering a fluid to a patient with an injector system during an imaging procedure.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

A system is disclosed herein to prevent the noise generated by a powered injector or other electrical equipment located in an operating room from being conducted via the patient (and then the ECG leads) to an ECG monitor. The system routes that noise from the patient through the filtering circuitry discussed hereinafter to ground. By filtering the noise before it reaches the ECG leads/monitor, the circuitry essentially suppresses the noise upon its appearance on the patient (i.e., immediately routes that noise from the patient to ground) and prevents it from reaching, and being received by, the ECG leads, and thus prevents the noise from distorting the ECG waveforms that are displayed on the monitor.

Figure 2:
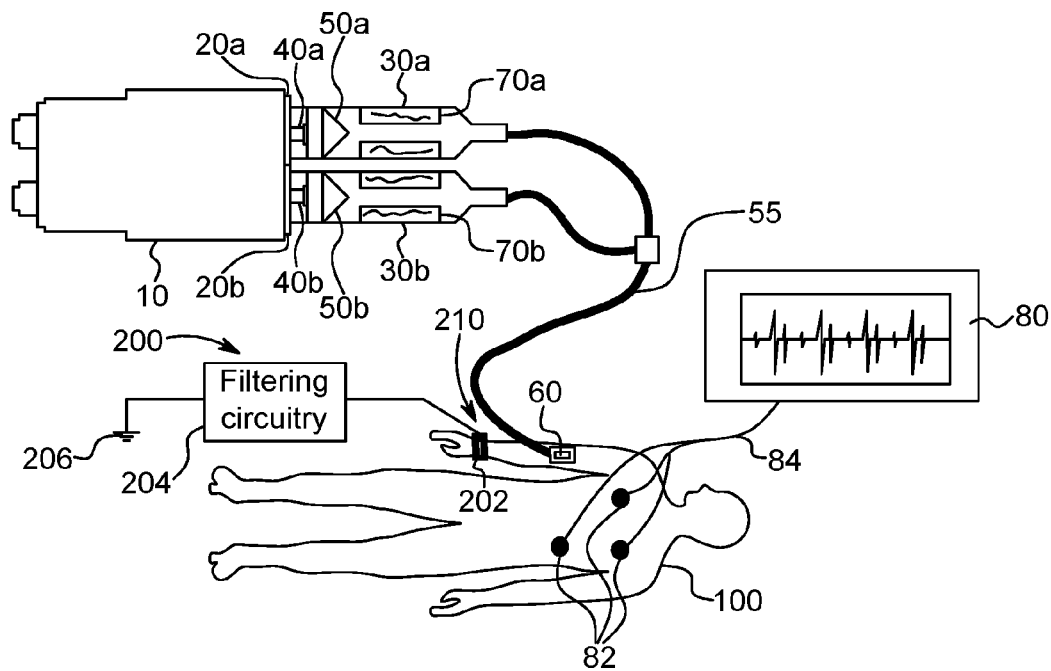
FIG. 2 is a schematic diagram of an arrangement for delivering a fluid to a patient with an injector system during an imaging procedure that includes a system for suppressing electrical noise in an ECG signal displayed on an ECG monitor in accordance with the present disclosure.

With specific reference to FIG. 2, a patient 100 undergoing a medical imaging procedure is positioned in a room that includes an imaging system (not shown) and an injection system for injecting contrast and/or saline into the patient. As discussed hereinabove, the injection system can include an injector 10, such as the MEDRAD® STELLANT® injector, that includes two syringe interfaces 20a and 20b to which two syringes 30a and 30b are removably attachable. Two drive members or pistons 40a and 40b operatively connect to plungers 50a and 50b slidably disposed in syringes 30a and 30b, respectively, to pressurize and inject the fluid therefrom into the patient 100 via a catheter 60 in fluid connection with syringes 30a and 30b. In addition, heater jackets 70a and 70b may be provided to maintain the fluid within the syringes 30a and 30b at a predetermined temperature. As shown in FIG. 2, such heater jackets 70a and 70b may each include an arcuate resistance heater portion configured to snap over the cylindrical body of the syringes 30a and 30b.

In many instances, a patient scheduled for a scanning procedure may also be connected to a vital signs monitoring system, such as an ECG monitor 80, via a plurality of electrodes 82 attached to the skin of the patient. Each electrode 82 is connected via a lead 84 to the ECG monitor 80. As discussed hereinabove, electrical noise/disturbance(s) are generated as a result of the use of the injector 10 and related equipment. For instance, electrical noise may be generated when the heater jackets 70a and 70b are turned on and off or due to an electrical disturbance (i.e., an ESD field) that may develop during the delivery of a fluid by the injector 10 due to the dissimilarities between the materials used for the barrels of the syringes 30a and 30b (e.g., plastic) and the plungers 50a and 50b (e.g., rubber). This electrical noise can be conveyed from the injector 10 and related equipment to the patient 100 via, for example, the fluid path 55 connecting the injector 10 to the catheter 60, which is conductive by virtue of the contrast medium or saline therein.

This noise will be picked up by the electrodes 82 of the ECG monitor 80 and cause a distortion of the ECG signal displayed on the ECG monitor 80 as shown in FIG. 1 unless the noise is routed to ground. Directly grounding the patient would allow for the greatest noise suppression. However, doing so could cause a hazardous condition of an electrical shock if the patient comes into contact with a high current conductor line in the vicinity of the patient. Accordingly, the system of the present disclosure suppresses noise by preventing DC currents from flowing while also providing an impedance to ground that limits the patient leakage current to under a maximum patient leakage current of 500 microamps, which is the maximum allowable current during a single fault under the IEC/EN 60601-1 standard.

Figure 3:
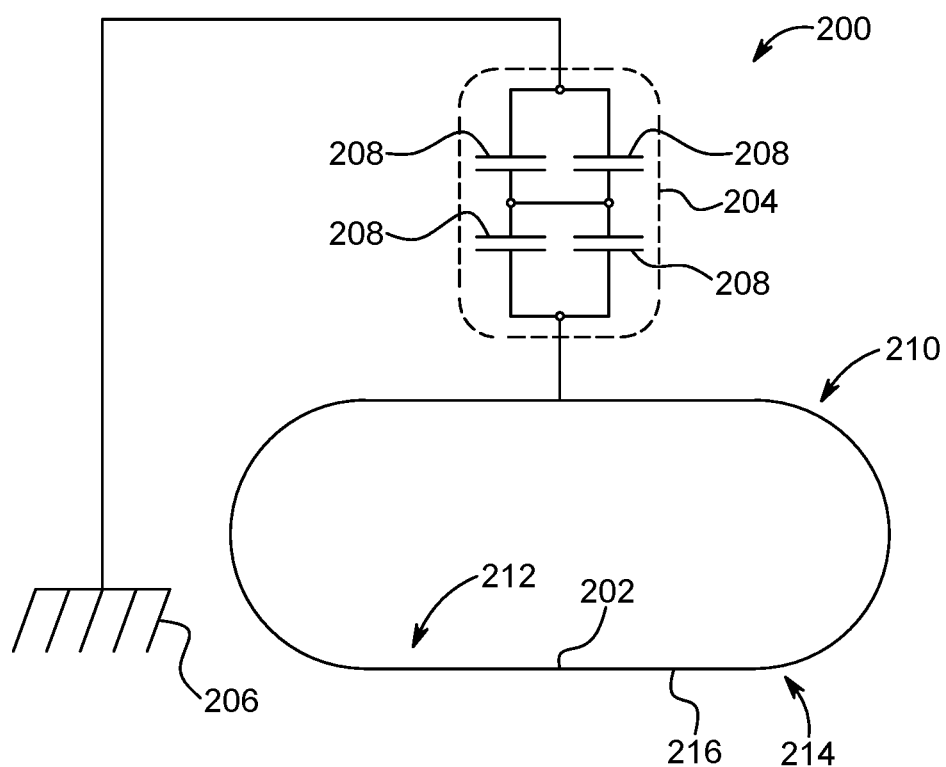
FIG. 3 is a schematic diagram of an example of the system for suppressing electrical noise in an ECG signal displayed on an ECG monitor in accordance with the present disclosure.

With reference to FIG. 3 and continued reference to FIG. 2, illustrated is a system, denoted generally as reference numeral 200, for suppressing electrical noise in an electrocardiogram (ECG) signal displayed on an ECG monitor 80. The system 200 includes a conductive material 202 provided in contact with a surface of the patient 100; and filtering circuitry 204 connected in series between the conductive material 202 and ground 206.

The filtering circuitry 204 is configured to filter to ground 206 the electrical noise present within the patient 100 that is generated by the injector 10 and associated equipment located near the patient 100. As can be seen from the output displayed on ECG monitor 80 in FIG. 2, the distortion 86 of the ECG signals displayed on the ECG monitor as shown in FIG. 1 have been removed because the noise generated by the injector 10 and the associated equipment has been effectively filtered to ground 206 by the filtering circuitry 204.

While the injector 10 and associated equipment is discussed herein as generating the electrical noise within the patient 100, this is not to be construed as limiting the present disclosure as the electrical noise may be generated by other electrical devices located near the patient 100 such as anesthesiology equipment or electrosurgical equipment. As can be seen from the output displayed on ECG monitor 80, the distortion 86 of the ECG signals displayed on the ECG monitor as shown in FIG. 1 have been removed because the noise generated by the injector 10 and the associated equipment has been effectively filtered to ground 206 by the filtering circuitry 204.

The filtering circuitry 204 may be configured as an array of capacitors 208. For instance, the array of capacitors 208 may include four capacitors arranged as shown in FIG. 3. The size of the capacitors 208 is chosen such that the capacitance is high enough to effectively filter the noise generated by the injector 10 while also maintaining an impedance that is high enough to limit the patient leakage current to under the maximum patient leakage current of 500 microamps. An exemplary value of the capacitance for each of the capacitors of the array of capacitors 208 is about 0.0047 µF. In addition, the configuration of the array of capacitors 208 shown in FIG. 3 was chosen to provide redundancy to the system. More specifically, by utilizing the configuration for the array of capacitors 208 shown in FIG. 3, if any one of the capacitors 208 fails, the filtering circuitry 204 will continue to function properly to filter noise.

While one example of the filtering circuitry 204 is specifically illustrated in FIG. 3, this is not to be construed as limiting the present disclosure as other arrangements for the filtering circuitry have been contemplated. For example, the filtering circuitry 204 may be configured as multiple strings of series capacitors, with those strings connected together in parallel.

With continued reference to FIGS. 2 and 3, the conductive material 202 of the system 200 may be provided as a bracelet or wrist strap, denoted generally as reference numeral 210, configured to be worn on a wrist of the patient 100. The conductive material 202 may be provided on an interior surface 212 of the bracelet 210 with an exterior surface 214 of the bracelet 210 made from an insulated material 216. The insulated material 216 may take the form of any suitable insulated material such as, but not limited to, plastics, paints, anodization, or other non-conductive surface treatments. While the use of a bracelet or wrist strap has been described hereinabove as providing a connection for the conductive material 202 to the patient 100, this is not to be construed as limiting the present disclosure as any suitable manner for providing a resistive connection between the conductive material 202 to the patient 100 may be utilized. For instance, the patient 100 may be required to wear a conductive gown that is operatively connected to the filtering circuitry 204.

The conductive material 202 may be manufactured from any suitable metallic material. In addition, the conductive material 202 is desirably non-magnetic so as not to interfere with medical imaging equipment such as that found within a Magnetic Resonance Imaging (MRI) suite. Examples of materials that can be utilized as conductive material 202 include, but are not limited to, non-magnetic austenitic stainless steel, aluminum or aluminum alloy with an anti-corrosive but electrically conductive surface treatment, copper with an anti-corrosive but electrically conductive surface treatment, a gold plating on a non-magnetic material, titanium or any other suitable material.

EXAMPLES

Figure 4:
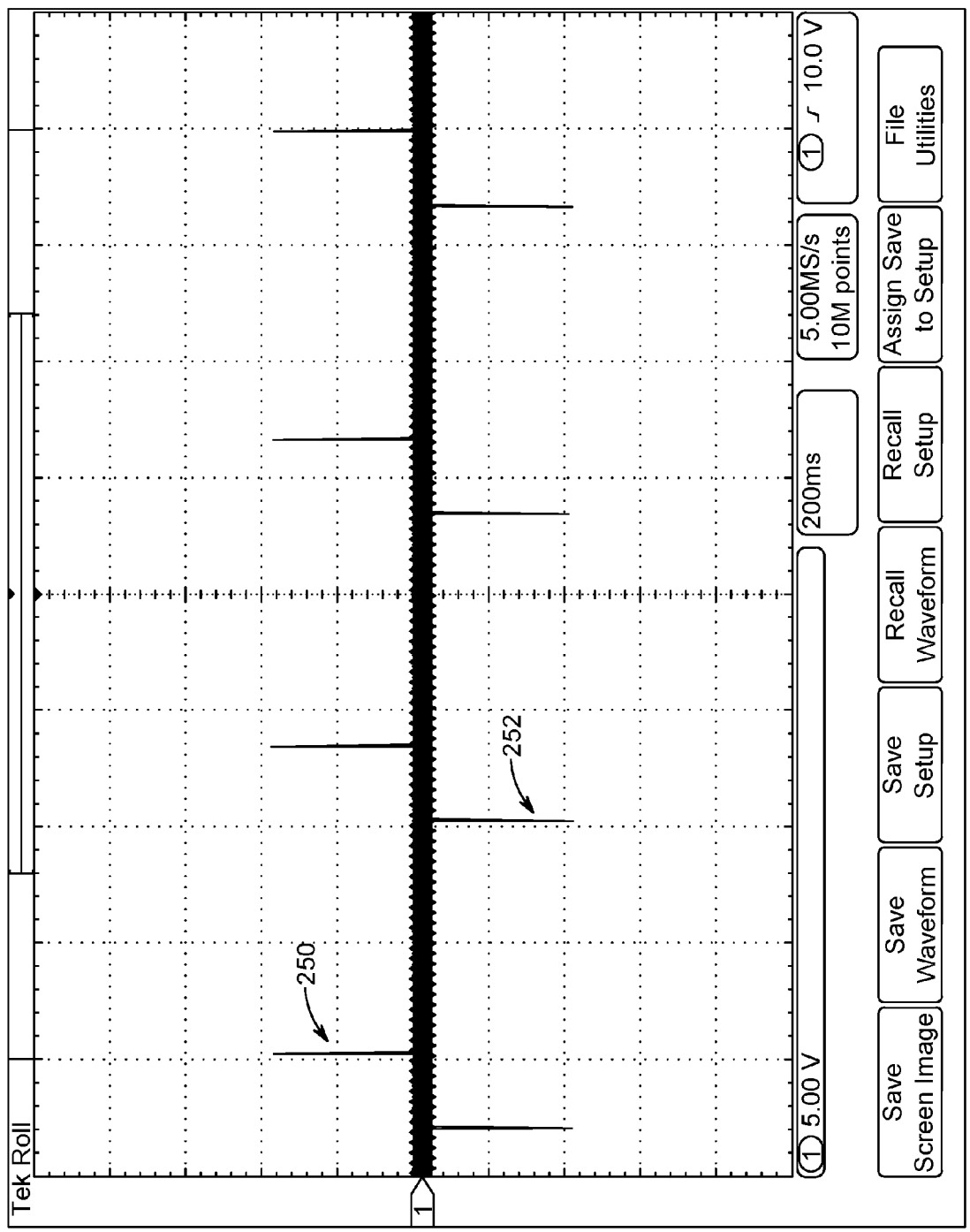
FIG. 4 is a waveform obtained that illustrates the noise generated when a heater jacket is turned on and off.
Figure 5:
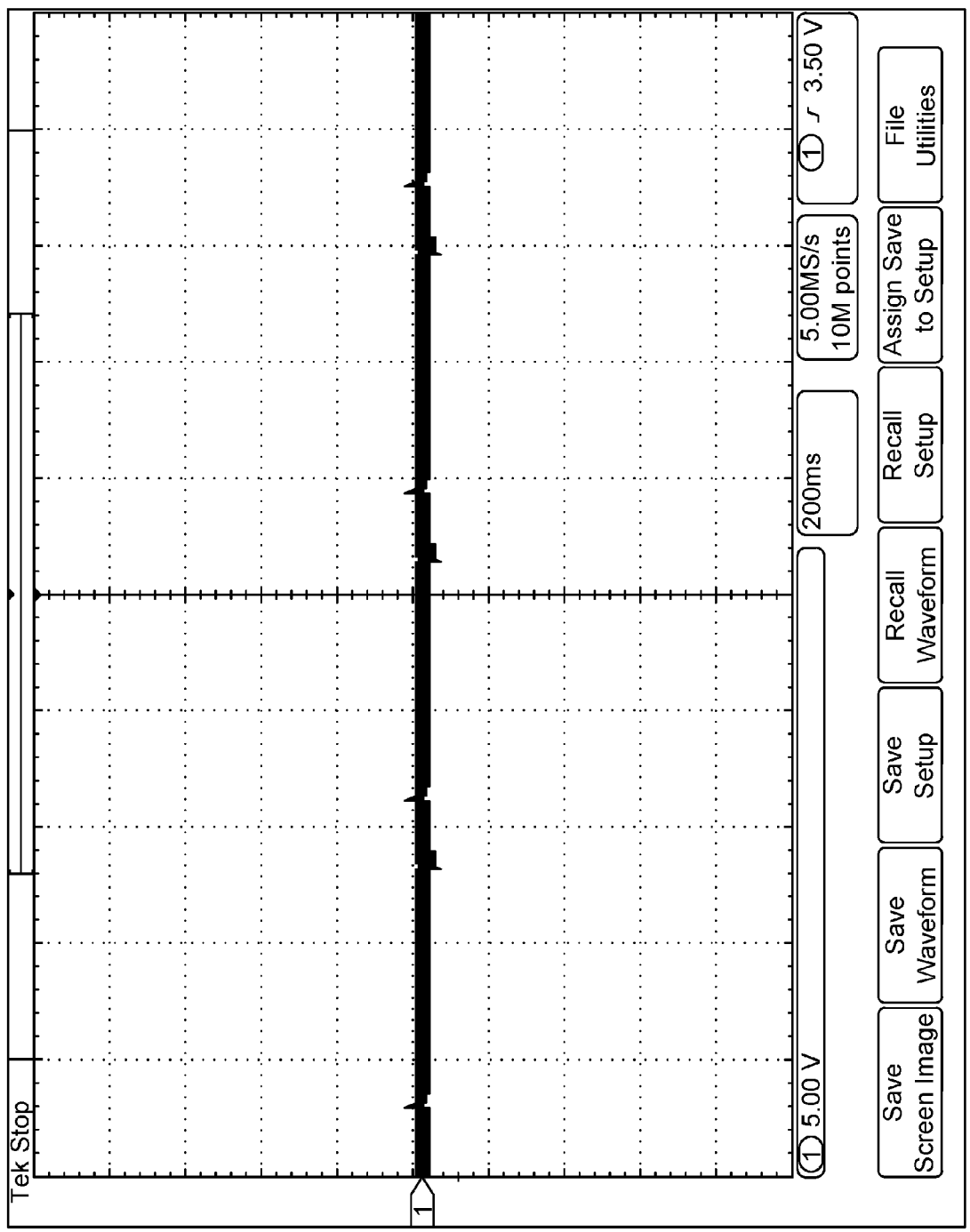
FIG. 5 is a waveform obtained that illustrates the manner in which the noise generated by the heating jacket is suppressed utilizing the system of the present disclosure.

As discussed hereinabove, one of the elements of the injection system that may generate electrical noise are the heater jackets 70a and 70b when they turn on and off. FIG. 4 is a waveform that illustrates the noise generated when a heater jacket is turned on and off (i.e., cycled). This noise is clearly shown by the spike 250 generated when the heater jackets 70a and 70b are turned on and the spike 252 generated when the heater jackets 70a and 70b are turned off. With reference to FIG. 5, another waveform was obtained when the heater jackets 70a and 70b were turned on and off. However, when this waveform was obtained, the patient 100 was connected to ground 206 via the filtering circuitry 204. As can be seen in the waveform illustrated in FIG. 5, the spikes 250 and 252 have been eliminated from the signal represented on the waveform.

Figure 6:
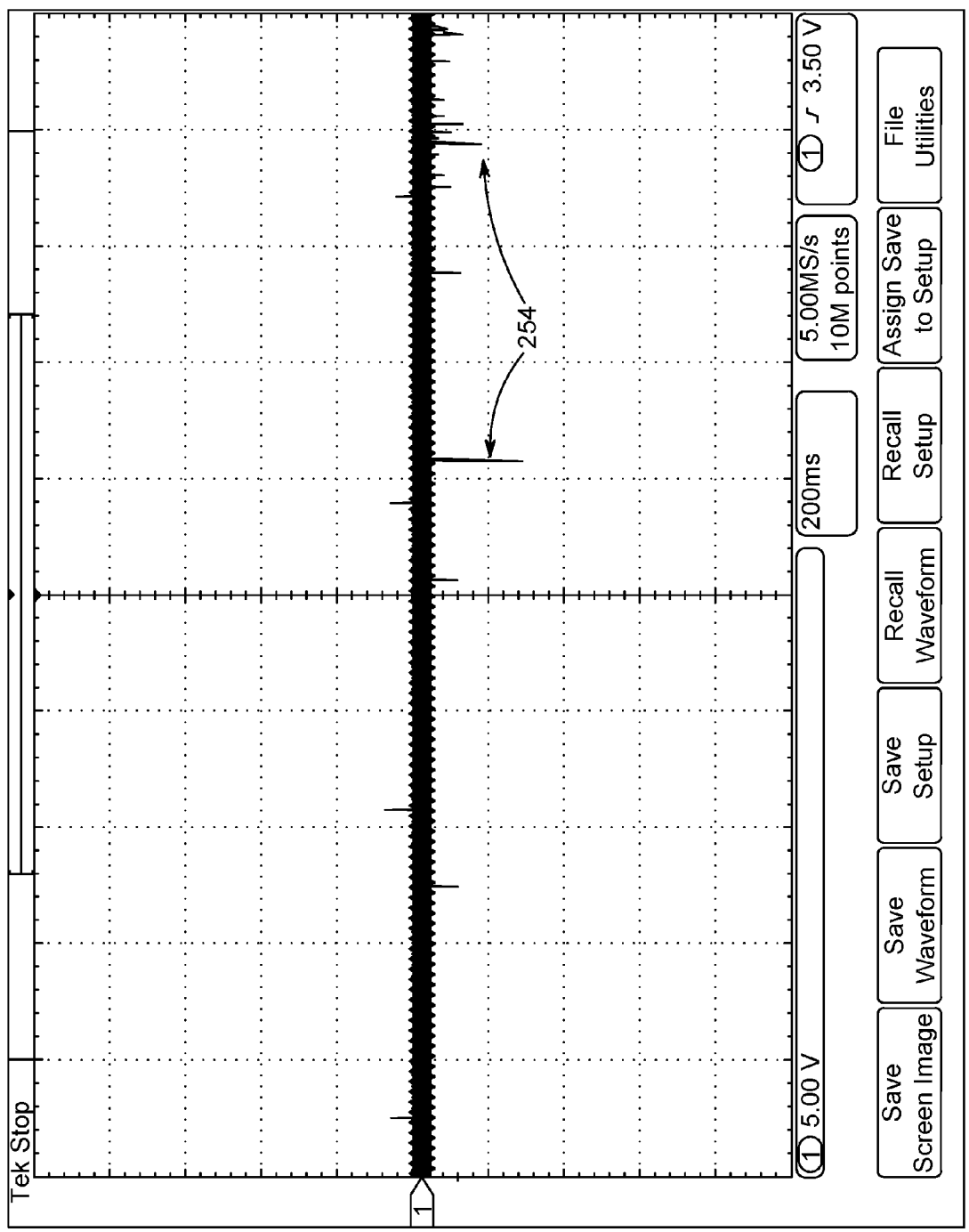
FIG. 6 is a waveform obtained that illustrates the noise generated due to an electrical disturbance that develops during the delivery of a fluid by the injector system due to the dissimilarities between the materials used for the barrels of the syringes and the plungers.
Figure 7:
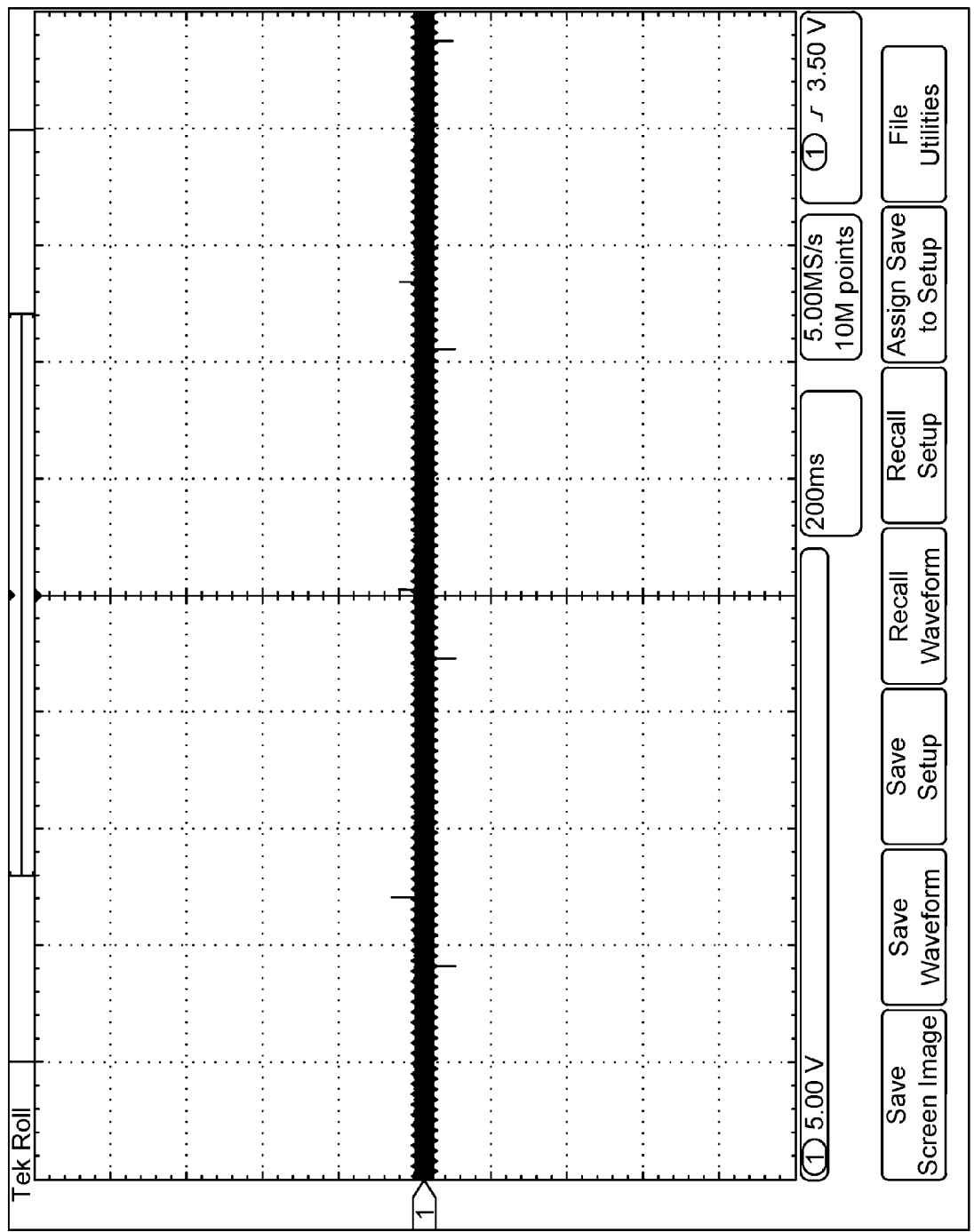
FIG. 7 is a waveform obtained that illustrates the manner in which the noise generated by the dissimilarities between the materials of the barrels of the syringes and the plungers is suppressed utilizing the system of the present disclosure.

Another element of the injection system that may generate electrical noise is an electrical disturbance that develops during the delivery of a fluid by the injector system due to the dissimilarities between the materials used for the barrels of the syringes 30a and 30b and the plungers 50a and 50b. FIG. 6 is a waveform that illustrates the noise generated during fluid delivery by the injection system due to the dissimilarities between the materials used for the barrels of the syringes 30a and 30b and the plungers 50a and 50b. This noise is clearly shown by the spikes 254 illustrated on the waveform. With reference to FIG. 7, another waveform was obtained during a fluid injection procedure with the injection system. However, when this waveform was obtained, the patient 100 was connected to ground 206 via the filtering circuitry 204. As can be seen in the waveform illustrated in FIG. 7, the spikes 254 have been eliminated from the signal represented on the waveform.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A system for suppressing electrical noise in an electrocardiogram (ECG) signal obtained by at least one electrode and displayed on an ECG monitor, the system comprising:

a conductive material distinct from the at least one electrode and configured to contact a surface of a patient; and filtering circuitry connected in series between the conductive material and ground, wherein the filtering circuitry is configured to filter to ground the electrical noise present within the patient such that the electrical noise is filtered before it is received by the at least one electrode and is prevented from distorting the ECG signal that is displayed on the ECG monitor.

2. The system of claim 1, wherein the electrical noise is generated by at least one electrical device located near the patient.

3. The system of claim 2, wherein the at least one electrical device is at least one of a powered injector, a heating device, anesthesiology equipment, and electrosurgical equipment.

4. The system of claim 1, wherein the conductive material is provided as a bracelet configured to be worn on a wrist of the patient.

5. The system of claim 4, wherein the conductive material is provided on an interior surface of the bracelet and an exterior surface of the bracelet is made from an insulated material.

6. The system of claim 1, wherein the conductive material is non-magnetic.

7. The system of claim 1, wherein the filtering circuitry is configured as an array of capacitors.

8. The system of claim 7, wherein the array of capacitors includes four capacitors.

9. The system of claim 8, wherein each of the capacitors of the array of capacitors has a capacitance of about 0.0047 μF.

10. A method for suppressing electrical noise in an electrocardiogram (ECG) signal obtained by at least one electrode and displayed on an ECG monitor, the method comprising:

providing a conductive material that is distinct from the at least one electrode and in contact with a surface of a patient;

providing filtering circuitry connected in series between the conductive material and ground; and filtering to ground, with the filtering circuitry, electrical noise present within the patient such that the electrical noise is filtered before it is received by the at least one electrode and is prevented from distorting the ECG signal that is displayed on the ECG monitor.

11. The method of claim 10, wherein the electrical noise is generated by at least one electrical device located near the patient.

12. The method of claim 11, wherein the at least one electrical device is at least one of a powered injector, a heating device, anesthesiology equipment, and electrosurgical equipment.

13. The method of claim 10, wherein the conductive material is provided as a bracelet configured to be worn on a wrist of the patient.

14. The method of claim 13, wherein the conductive material is provided on an interior surface of the bracelet and an exterior surface of the bracelet is made from an insulated material.

15. The method of claim 10, wherein the conductive material is non-magnetic.

16. The method of claim 10, wherein the filtering circuitry is configured as an array of capacitors.

17. The method of claim 16, wherein the array of capacitors includes four capacitors.

18. The method of claim 17, wherein each of the capacitors of the array of capacitors has a capacitance of about 0.0047 μF.

19. A system for suppressing electrical noise in an electrocardiogram (ECG) signal obtained by at least one electrode and displayed on an ECG monitor, the system comprising:

a wrist strap positioned around a wrist of a patient and comprising a conductive material distinct from the at least one electrode and configured to contact a surface of the patient; and filtering circuitry comprising an array of capacitors connected in series between the conductive material of the wrist strap and ground, wherein the filtering circuitry is configured to filter to ground the electrical noise present within the patient that is generated by at least one electrical device located near the patient such that the electrical noise is filtered before it is received by the at least one electrode and is prevented from distorting the ECG signal that is displayed on the ECG monitor.

20. The system of claim 19, wherein the at least one electrical device is at least one of a powered injector, a heating device, anesthesiology equipment, and electrosurgical equipment.

* * * * *